United States Patent [19]

VandenBerg

[11] Patent Number: Plant 6,801

[45] Date of Patent: May 16, 1989

[54] CHRYSANTHEMUM PLANT NAMED DARK BRONZE CHARM

[75] Inventor: Cornelis P. VandenBerg, Salinas, Calif.

[73] Assignee: Yoder Brothers, Inc., Barberton, Ohio

[21] Appl. No.: 135,295

[22] Filed: Dec. 21, 1987

[51] Int. Cl.[4] ..... A01H 5/00

[52] U.S. Cl. ..... Plt./79

[58] Field of Search ..... Plt./79

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Dark Bronze Charm particularly characterized by its flat capitulum form; decorative capitulum type; orange-bronze ray floret color; diameter across face of capitulum of up to 11 cm at maturity when grown as a pinched disbudded port mum; uniform eight week photoperiodic flowering response to short days; medium plant height when grown as a pinched pot mum; and spreading branching pattern.

3 Drawing Sheets

The present invention comprises a new and distinct cultivar of Chrysanthemum, botanically known as *Chrysanthemum morifolium,* Ramat., and referred to by the cultivar name Dark Bronze Charm.

Dark Bronze Charm, identified as 85302054, is a spontaneous mutation of the cultivar Salmon Charm, disclosed in applicant's U.S. Plant Pat. No. 6,334.

Dark Bronze Charm was discovered and selected by a technician working under formulations established by Cornelis P. VandenBerg on July 30, 1985, in a controlled environment in Leamington, Ontario, Canada as one flowering plant within a flowering block of the cultivar Salmon Charm.

The first act of asexual reproduction of Dark Bronze Charm was accomplished when vegetative cuttings were taken from the initial selection in October of 1985 in a controlled environment in Leamington, Ontario, Canada, by technicians working under formulations established by Cornelis P. VandenBerg.

Horticultural examination of controlled flowerings of successive plantings has shown that the unique combination of characteristics as herein disclosed for Dark Bronze Charm are firmly fixed and are retained through successive generations of asexual reproduction.

Dark Bronze Charm has not been observed under all possible environmental conditions. The penotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dark Bronze Charm, which, in combination, distinguish this Chrysanthemum as a new and distinct cultivar:

1. Flat capitulum form.
2. Decorative capitulum type.
3. Orange-bronze ray floret color.
4. Diameter across face of capitulum of up to 11 cm at maturity, when grown as a pinched disbudded pot mum.
5. Uniform eight week photoperiodic flowering response to short days.

6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Spreading branching pattern.

The accompanying photographic drawings show typical inflorescence and leaf characteristics of Dark Bronze Charm, with the colors being as nearly true as possible with illustrations of this type.

Sheet 1 is a color photograph of Dark Bronze Charm grown as a pinched disbudded pot mum.

Sheet 2 is a black and white photograph of three views of the inflorescence of Dark Bronze Charm.

Sheet 3 is a black and white photograph showing the upper and under sides of the leaves of Dark Bronze Charm at three stages of development (mature, intermediate and immature).

Of the commercial cultivars known to the inventor, the most similar in comparison to Dark Bronze Charm is Bronze Charm, disclosed in applicant's U.S. Plant Pat. No. 6,314. All traits of Dark Bronze Charm are similar to those of Bronze Charm, except the color of ray florets. Color of ray florets of Dark Bronze Charm is a bright lively orange-bronze, upgrading the somewhat dull bronze color of Bronze Charm.

In the following description, color references are made to The Royal Horticultural Society Colour Chart. The exact color for corolla of ray florets of Dark Bronze Charm is not represented in the R.H.S. Colour Chart, and the color values given are those closest to the actual color of Dark Bronze Charm. The color values were determined on plant material grown as a pinched disbudded pot mum in Salinas, Calif. on June 11, 1987.

Classification:

*Botanical.*—*Chrysanthemum morifolium,* Ramat., cv. Dark Bronze Charm.

*Commercial.*—Decorative disbudded pot mum.

INFLORESCENCE

A. Capitulum:

*Form.*—Flat.

*Type.*—Decorative.

*Diameter across face.*—Up to 11 cm at maturity.

B. Corolla of ray florets:

*Color (general tonality from a distance of three meters).*—Orange-bronze.

*Color (upper surface).*—167B to 168C.

*Color (under surface).*—164C.

*Shape.*—Flat, oblong.

C. Corolla of disc florets:

*Color (mature).*—154B to 154C.

*Color (immature).*—149B.

D. Reproductive organs:

*Androecium.*—Present on disc florets only, very few; scant pollen.

*Gynoecium.*—Present on both ray and disc florets.

PLANT

A. General appearance:

*Height.*—Medium; 25 to 35 cm as a pinched disbudded pot mum with 0 to 7 long days after pinch prior to short days and 1 application of 2500 ppm B-9 SP.

*Branching pattern.*—Spreading.

B. Foliage:

*Color (upper surface).*—147A.

*Color (under surface).*—147B.

*Shape.*—Lobed and serrated.

I claim:

1. A new and distinct Chrysanthemum plant named Dark Bronze Charm, as described and illustrated, and parts thereof.

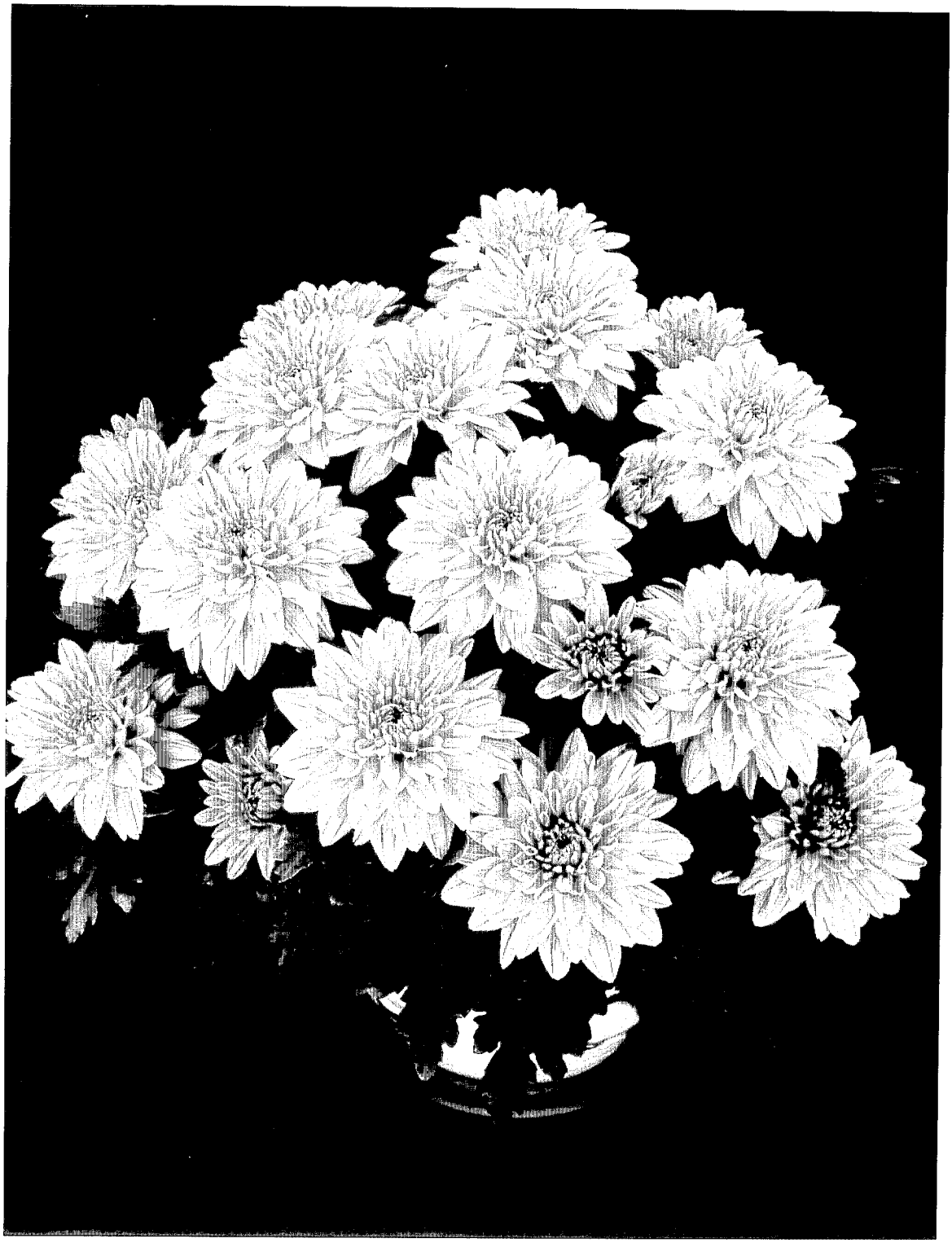

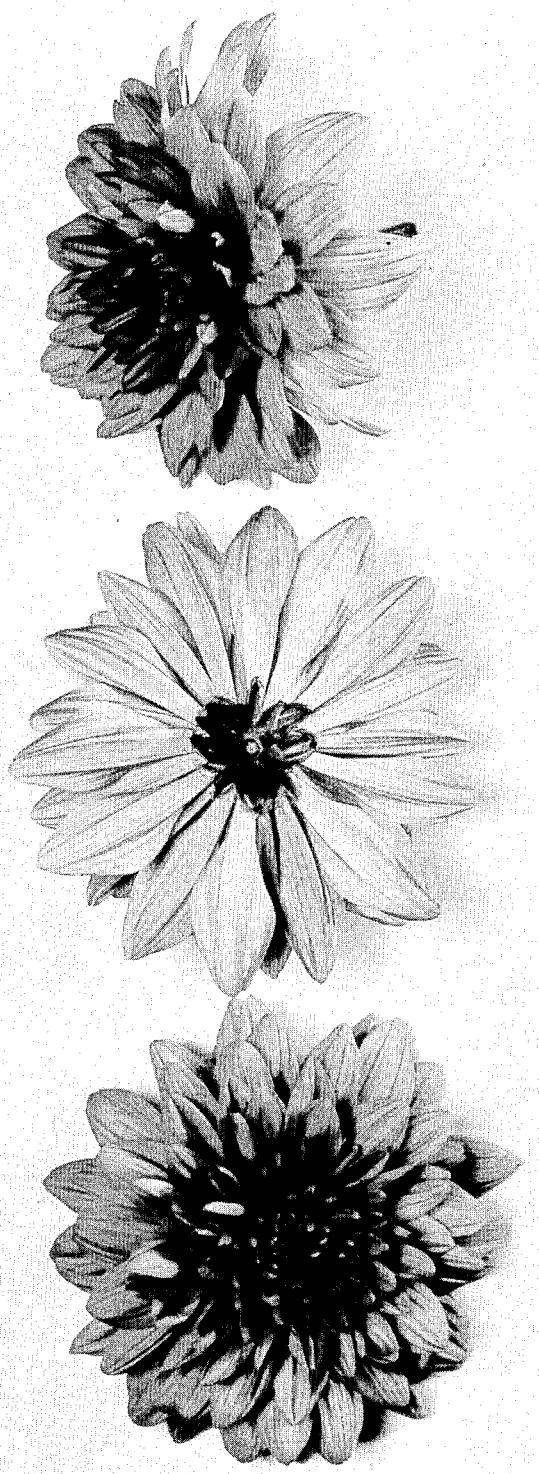

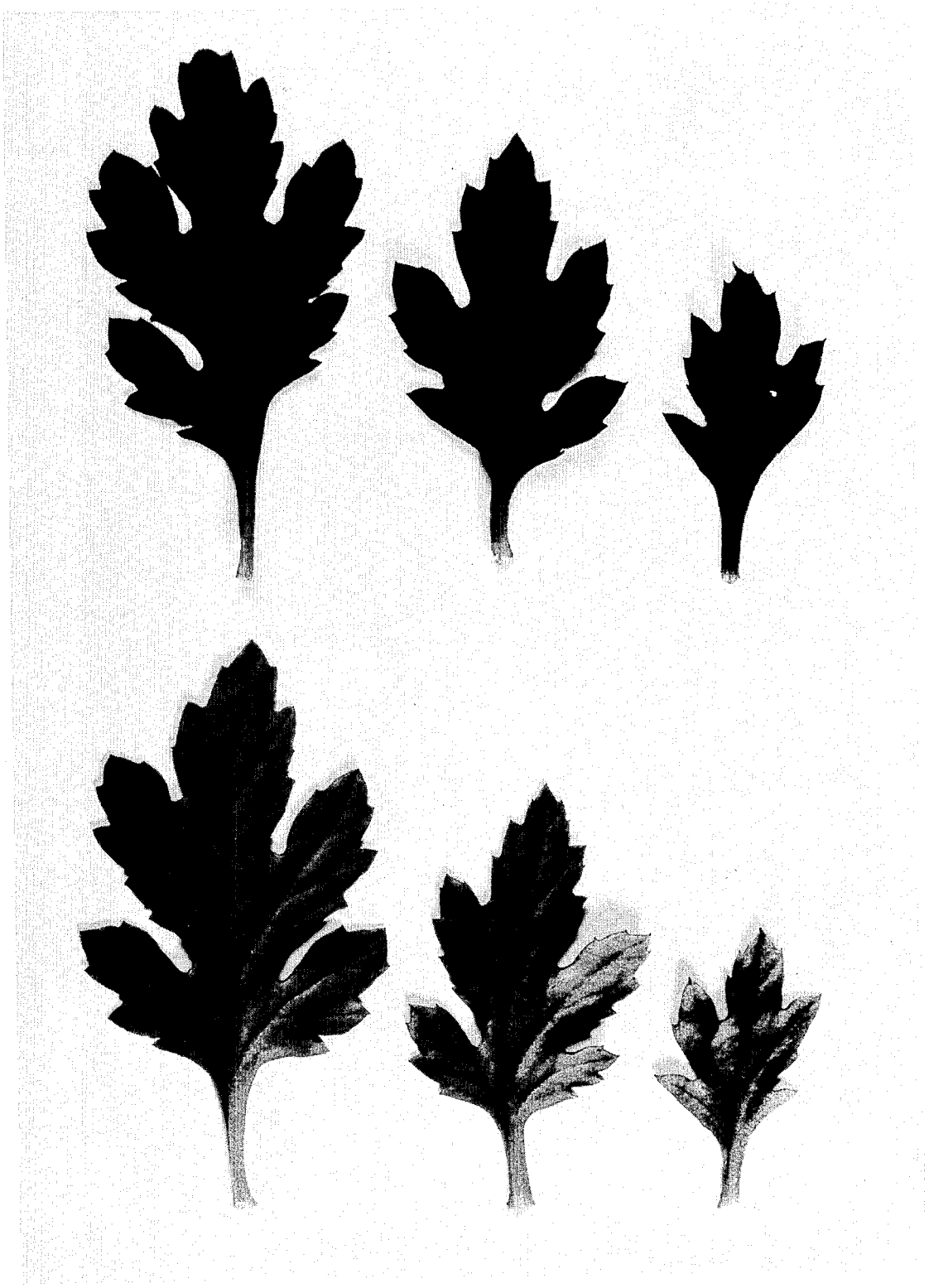

* * * * *